(12) United States Patent
Majumdar et al.

(10) Patent No.: US 11,461,338 B2
(45) Date of Patent: Oct. 4, 2022

(54) METHODS AND SYSTEMS FOR VISUALIZING DATA QUALITY

(71) Applicant: LIFE TECHNOLOGIES CORPORATION, Carlsbad, CA (US)

(72) Inventors: Nivedita Sumi Majumdar, San Bruno, CA (US); Harrison Leong, San Francisco, CA (US); Theodore E. Straub, Burlingame, CA (US); David Hoard, Escondido, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 723 days.

(21) Appl. No.: 14/392,323

(22) PCT Filed: Jun. 27, 2014

(86) PCT No.: PCT/US2014/044732
§ 371 (c)(1),
(2) Date: Dec. 24, 2015

(87) PCT Pub. No.: WO2014/210559
PCT Pub. Date: Dec. 31, 2014

(65) Prior Publication Data
US 2016/0275149 A1    Sep. 22, 2016

Related U.S. Application Data

(60) Provisional application No. 61/841,167, filed on Jun. 28, 2013.

(51) Int. Cl.
*G06F 16/2457* (2019.01)
*G06F 16/248* (2019.01)
*G16B 45/00* (2019.01)

(52) U.S. Cl.
CPC ...... *G06F 16/24575* (2019.01); *G06F 16/248* (2019.01); *G16B 45/00* (2019.02)

(58) Field of Classification Search
CPC ......... G06F 17/30528; G06F 17/30554; G06F 19/26; G06F 16/24575; G06F 16/248; G16B 45/00
(Continued)

(56) References Cited

U.S. PATENT DOCUMENTS

| 8,572,506 B2 | 10/2013 | Janaway et al. |
| 10,726,589 B2 | 7/2020 | Leong et al. |

(Continued)

FOREIGN PATENT DOCUMENTS

| CN | 1694967 A | 11/2005 |
| CN | 102465174 A | 5/2012 |

(Continued)

OTHER PUBLICATIONS

Digital PCR Analysis Software version 3, Fluidigm User Guide, 2011, pp. 1-91 (Year: 2011).*

(Continued)

*Primary Examiner* — Tony Mahmoudi
*Assistant Examiner* — Kamal K Dewan
(74) *Attorney, Agent, or Firm* — Jones Robb, PLLC

(57) ABSTRACT

A method for generating a data visualization is provided. The method includes receiving a plurality of data points related to fluorescent emissions values from a plurality of reaction sites. The fluorescent emission values include information for a first type of dye and a second type of dye. The method further includes displaying a first portion of the plurality of data points related to the first type of dye in a representation of location of the plurality of reaction sites, and displaying a second portion of the plurality of data points related to the second type of dye in the representation.

(Continued)

The method further includes displaying the first portion of the plurality of data points in a scatter plot display. The scatter plot shows fluorescent values related to the first dye on the y-axis and fluorescent values related to the second dye on the x-axis. The method includes displaying the second portion of the plurality of data points in the scatter plot display.

19 Claims, 13 Drawing Sheets

(58) Field of Classification Search
USPC ........... 707/722, 999.102, 999.006, E17.093; 382/133, 129
See application file for complete search history.

(56) References Cited

U.S. PATENT DOCUMENTS

| | | | |
|---|---|---|---|
| 10,777,303 B2 | 9/2020 | Majumdar | |
| 2002/0067358 A1 | 6/2002 | Casari et al. | |
| 2003/0030637 A1* | 2/2003 | Grinstein | G16B 45/00 345/420 |
| 2003/0143554 A1* | 7/2003 | Berres | G06F 19/18 435/6.18 |
| 2004/0133313 A1* | 7/2004 | Kuhn | G16B 30/00 700/266 |
| 2004/0033601 A1 | 12/2004 | Davidson | |
| 2005/0019792 A1 | 1/2005 | McBride et al. | |
| 2005/0079603 A1* | 4/2005 | Sandstrom | B82Y 30/00 435/288.7 |
| 2005/0119534 A1 | 6/2005 | Trost et al. | |
| 2006/0004526 A1* | 1/2006 | Hadd | G06F 19/26 702/20 |
| 2007/0027637 A1* | 2/2007 | Delenstarr | G16B 25/00 702/23 |
| 2007/0255506 A1 | 11/2007 | Lobban et al. | |
| 2008/0057499 A1* | 3/2008 | Fu | C12Q 1/6858 435/6.14 |
| 2008/0075380 A1* | 3/2008 | Dube | G06T 7/0012 382/255 |
| 2008/0154512 A1* | 6/2008 | Leong | C12Q 1/6851 702/19 |
| 2008/0168151 A1 | 7/2008 | Fuchs et al. | |
| 2009/0047679 A1* | 2/2009 | Shain | C12Q 1/6851 435/6.11 |
| 2010/0191678 A1* | 7/2010 | Steed | G06T 11/206 706/11 |
| 2011/0191343 A1 | 8/2011 | Heaton et al. | |
| 2011/0207624 A1* | 8/2011 | Shen | C12Q 1/6869 506/9 |
| 2011/0244455 A1* | 10/2011 | Larson | C12Q 1/686 435/6.11 |
| 2011/0250597 A1 | 10/2011 | Larson et al. | |
| 2011/0252353 A1* | 10/2011 | Janaway | G06F 19/18 715/771 |
| 2011/0287951 A1* | 11/2011 | Emmert-Buck | B01L 3/5025 506/7 |
| 2012/0078601 A1 | 3/2012 | Avinash et al. | |
| 2012/0089917 A1 | 4/2012 | Kwahk et al. | |
| 2012/0107824 A1* | 5/2012 | Latham | C12Q 1/6858 435/6.12 |
| 2013/0310260 A1* | 11/2013 | Kim | G16B 30/00 506/2 |
| 2014/0045712 A1* | 2/2014 | Link | C12Q 1/686 506/9 |
| 2014/0087386 A1* | 3/2014 | Chiu | C12Q 1/6806 435/6.12 |
| 2014/0107937 A1* | 4/2014 | Kanderian | G16B 20/00 702/20 |
| 2014/0154787 A1* | 6/2014 | Sun | C12Q 1/686 435/287.2 |
| 2014/0372953 A1* | 12/2014 | Laurance | G06F 3/04817 715/835 |
| 2015/0247190 A1* | 9/2015 | Ismagilov | C12Q 1/6851 506/9 |
| 2016/0224724 A1* | 8/2016 | Zhao | G16B 20/10 |
| 2017/0002400 A1* | 1/2017 | Hutchison | C12Q 1/686 |
| 2018/0225415 A1 | 8/2018 | Majumdar | |
| 2021/0042972 A1 | 2/2021 | Leong et al. | |

FOREIGN PATENT DOCUMENTS

| | | |
|---|---|---|
| CN | 103038774 A | 4/2013 |
| EP | 3014506 | 1/2020 |
| WO | 2012/082464 A2 | 6/2012 |
| WO | 2013074204 A2 | 5/2013 |
| WO | 2014/074735 A2 | 5/2014 |

OTHER PUBLICATIONS

Benjamin Hindson et al, "High-Throughput Droplet Digital PCR System for Absolute Quantitation of DNA Copy Number", Published Oct. 28, 2011, pp. 8604-8610 (Year: 2011).*
International Preliminary Report on Patentablity and Written Opinion issued in International application No. PCT/US2014/044732, dated Dec. 29, 2015.
"Digital PCR Analysis Software version 3", Jun. 18, 2011 (Jun. 18, 2011), pp. 1-90, XP055103593, Retrieved from the Internet: URL:http://web.archive.org/web/20140221083230/http://filestorage.iddrc.com/molecular-genetics/DigitalPCRAnalysisUserGuide.pdf, retrieved on Feb. 21, 2014.
CN Office Action issued in corresponding Chinese Application No. 201380069424.7, dated Apr. 13, 2020.
Belder et al., "Surface Modification in Microchip Electrophoresis," Electrophoresis, 24:3595-3606 (2003).
Chinese Supplementary Search Report issued in Chinese Application No. 2013800694247, dated Jul. 3, 2019.
European Communication issued in Application No. 13 799 705.2, dated Jan. 31, 2019.
DPIot Graph Software for Scientists and Engineer, Oct. 7, 2011.
"Applied Biosystems StepOne and StepOnePlus Real-Time PCR Systems for Genotyping Experiments", Getting Started Guide, Jun. 2010, 1-156.
International Preliminary Report on Patentability and Written Opinion for Application No. PCT/US2013/068984, dated May 21, 2015, 15 pages.
International Search Report and Written Opinion of the ISA for Int'l Application No. PCT/US2013/068984, dated Jun. 12, 2014.
Whale, Alexandra S. et al., "Comparison of Microfluidic Digital PCR and Conventional Quantitative PCR for Measuring Copy Number Variation", Nucleic Acids Research, vol. 40, No. 11, e82, Feb. 2012, 1-9.
Zhong, Qun et al., "Multiplex Digital PGR: breaking the one target per color barrier of quantitative PCR", Lab on a Chip, vol. 11, 2011, 2167-2174.
EP3014506B1, Opposition Brief of Patentee, Mar. 11, 2021.
EP3014506B1, Notice of Opposition Annex 1, Oct. 21, 2020.
EP3014506B1, Notice of Opposition, Oct. 21, 2020.
EP3014506B1, Consolidated List of Citations, Jan. 5, 2021.
EP3014506, Opposition—Response to Proprieter, dated Oct. 22, 2021.
EP3014506, Opposition—Transmittal of Decision, dated Nov. 12, 2021.
EP3014506, Written Submission in Preparation to During Oral Proceedings, dated Apr. 7, 2022.
EP3014506, Brief Communication—Opposition Proceedings, dated Apr. 13, 2022.
U.S. Appl. No. 61/723,732, filed Nov. 7, 2012.
U.S. Appl. No. 61/803,010, filed Mar. 18, 2013.

* cited by examiner

METHODS AND SYSTEMS FOR VISUALIZING DATA QUALITY

BACKGROUND

Systems for biological and biochemical reactions have been used to monitor, measure, and/or analyze such reactions in real time. Such systems are commonly used in sequencing, genotyping, polymerase chain reaction (PCR), and other biochemical reactions to monitor the progress and provide quantitative data.

Currently, there is an increasing demand to provide greater numbers of reactions per test or experiment have resulted in instruments that are able to conduct ever higher numbers of reactions simultaneously. The increase in the number sample sites in a test or experiment has led to microtiter plates and other sample formats that provide ever smaller sample volumes. In addition, techniques such as digital PCR (dPCR) have increased the demand for smaller sample volumes that contain either zero or one target nucleotide sequence in all or the majority of a large number of test samples.

Digital PCR may be used to detect and quantify the concentration of rare alleles, to provide absolute quantitation of nucleic acid samples, and to measure low fold-changes in nucleic acid concentration. Generally, increasing the number of replicates increases the accuracy and reproducibility of dPCR results.

In dPCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the samples containing the target nucleotide sequence are amplified and produce a positive detection signal, while the samples containing no target nucleotide sequence are not amplified and produce no detection signal.

For further analysis, the immense number of data points the data collected from a dPCR experiment is challenging to organize and visualize in a manner that is useful to a user.

SUMMARY

In one exemplary embodiment, a method for generating a data visualization is provided. The method includes receiving a plurality of data points related to fluorescent emissions values from a plurality of reaction sites. The fluorescent emission values include information for a first type of dye and a second type of dye. The method further includes displaying a first portion of the plurality of data points related to the first type of dye in a representation of location of the plurality of reaction sites, and displaying a second portion of the plurality of data points related to the second type of dye in the representation. The method further includes displaying the first portion of the plurality of data points in a scatter plot display. The scatter plot shows fluorescent values related to the first dye on the y-axis and fluorescent values related to the second dye on the x-axis. The method includes displaying the second portion of the plurality of date points in the scatter plot display.

DETAILED DESCRIPTION

Figure 1:
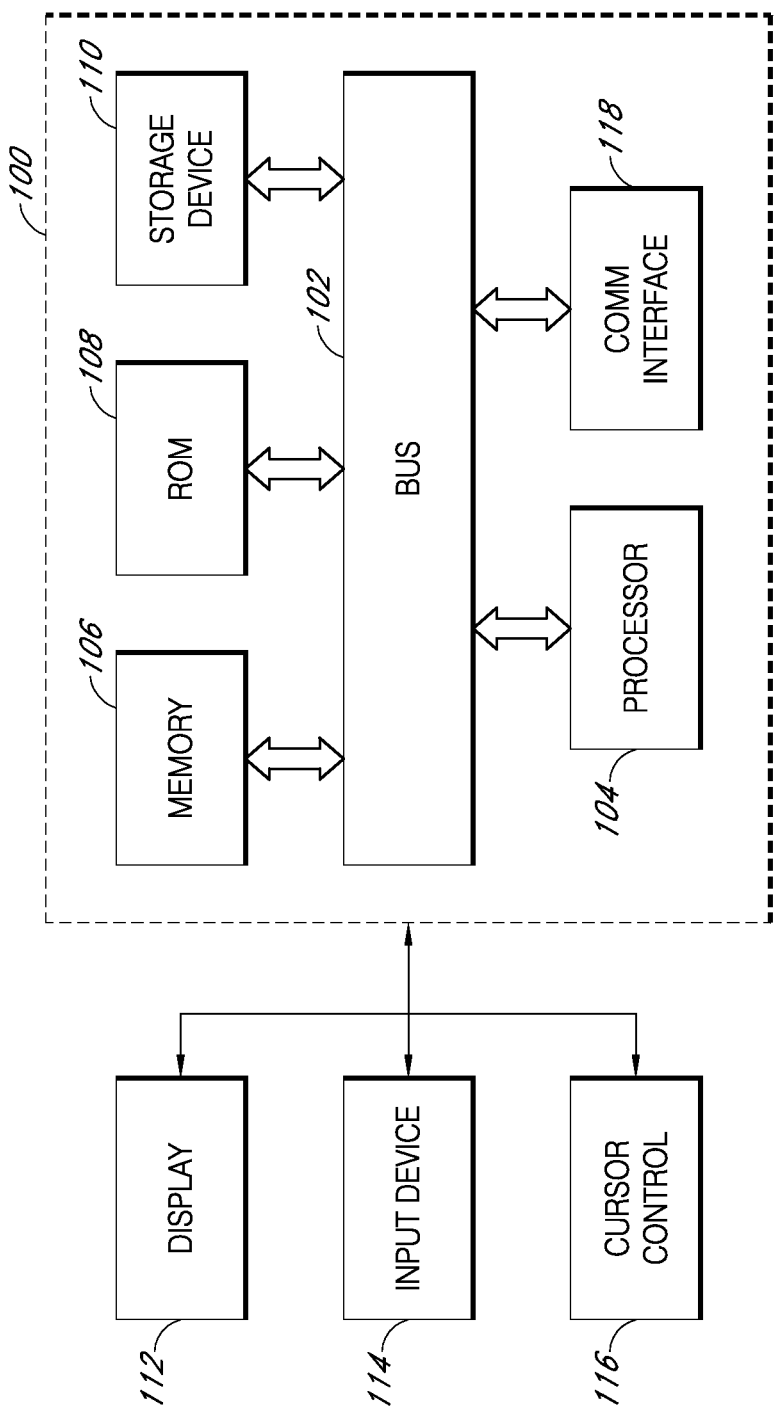
FIG. 1 illustrates an exemplary computing system that various embodiments described herein may be implemented.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

In various embodiments, the devices, instruments, systems, and methods described herein may be used to detect one or more types of biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example.

As described below, in accordance with various embodiments described herein, reaction sites may include, but are not limited to, through-holes, wells, indentations, spots, cavities, sample retainment regions, and reaction chambers, for example.

Furthermore, as used herein, thermal cycling may include using a thermal cycler, isothermal amplification, thermal convention, infrared mediated thermal cycling, or helicase dependent amplification, for example. In some embodiments, the chip may be integrated with a built-in heating element. In various embodiments, the chip may be integrated with semiconductors.

According to various embodiments, detection of a target may be, but is not limited to, fluorescence detection, detection of positive or negative ions, pH detection, voltage detection, or current detection, alone or in combination, for example.

Various embodiments described herein are particularly suited for digital PCR (dPCR). In digital PCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal. Using Poisson statistics, the number of target nucleotide sequences in the original solution may be correlated to the number of samples producing a positive detection signal.

In order to conduct a typical dPCR protocol, procedure, or experiment, it is advantageous to be able to divide an initial sample solution into tens of thousands or hundreds of thousands of test samples each having a volume of several nanoliters, at or about one nanoliter, or less than one nanoliter, in a way that is simple and cost effective. Because the number of target nucleotide sequences may be very small, it may also be important in such circumstances that the entire content of the initial solution be accounted for and contained in the plurality of reaction sites.

Embodiments described herein solve these and other dPCR design constraints by distributing an initial sample solution into a plurality of reaction sites in a way that accounts for all, or essentially all, of sample solution.

In various embodiments, the devices, instruments, systems, and methods described herein may be used to detect one or more types of biological components of interest. These biological components of interest may include, but are not limited to, DNA sequences, RNA sequences, genes, oligonucleotides, or cells (e.g., circulating tumor cells). In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation.

As described above, digital PCR technology generates thousands of data points. It is useful for a user to be able to visualize the data in order to quickly and easily know information about their experiment such as a preliminary indication of useful data or good quality data. New graphical techniques are required to allow people to review and manipulate the data.

In various embodiments of the present teachings, data may be displayed at a special location. For example, data may be displayed to the user in two-dimensions (x,y coordinates). Data may also be displayed so that a quality value is apparent to the user indicating good to bad quality data. In yet other embodiments, different dyes associated with the data may be displayed. For example, data associated with the FAM dye and data associated with the VIC dye may be indicated so that a user may be able to visualize the results. In other embodiments, positive and negative calls the processing system has determined associated with the data points may be visualized.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

FIG. 1 is a block diagram that illustrates a computer system 100 that may be employed to carry out processing functionality, according to various embodiments, upon which embodiments of a thermal cycler system (not shown) may utilize. Computing system 100 can include one or more processors, such as a processor 104. Processor 104 can be implemented using a general or special purpose processing engine such as, for example, a microprocessor, controller or other control logic. In this example, processor 104 is connected to a bus 102 or other communication medium.

Further, it should be appreciated that a computing system 100 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 100 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 100 may include bus 102 or other communication mechanism for communicating information, and processor 104 coupled with bus 102 for processing information.

Computing system 100 also includes a memory 106, which can be a random access memory (RAM) or other dynamic memory, coupled to bus 102 for storing instructions to be executed by processor 104. Memory 106 also may be used for storing temporary variables or other intermediate information during execution of instructions to be executed by processor 104. Computing system 100 further includes a read only memory (ROM) 108 or other static storage device coupled to bus 102 for storing static information and instructions for processor 104.

Computing system 100 may also include a storage device 110, such as a magnetic disk, optical disk, or solid state drive (SSD) is provided and coupled to bus 102 for storing information and instructions. Storage device 110 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 110 may include other similar instrumentalities for allowing computer programs or other instructions or data to be loaded into computing system 100. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 110 to computing system 100.

Computing system 100 can also include a communications interface 118. Communications interface 118 can be used to allow software and data to be transferred between computing system 100 and external devices. Examples of communications interface 118 can include a modem, a network interface (such as an Ethernet or other NIC card), a communications port (such as for example, a USB port, a RS-232C serial port), a PCMCIA slot and card, Bluetooth, etc. Software and data transferred via communications interface 118 are in the form of signals which can be electronic, electromagnetic, optical or other signals capable of being received by communications interface 118. These signals may be transmitted and received by communications interface 118 via a channel such as a wireless medium, wire or cable, fiber optics, or other communications medium. Some examples of a channel include a phone line, a cellular phone link, an RF link, a network interface, a local or wide area network, and other communications channels.

Computing system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104, for example. An input device may also be a display, such as an LCD display, configured with touchscreen input capabilities. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A computing system 100 provides data processing and provides a level of confidence for such data. Consistent with certain implementations of embodiments of the present teachings, data processing and confidence values are provided by computing system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 104 for execution. Such instructions, generally referred to as "computer program code" (which may be grouped in the form of computer programs or other groupings), when executed, enable the computing system 100 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computing system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Color Coding by a Continuous Variable

According to various embodiments of the present teachings, a user may view the spatial distribution of the data by a quality value to examine the statistical distribution of FAM and VIC, for example. The user may then be able to select the data by way of the quality value.

A quality value may be a numerical value, determined by a processor, indicating the quality of the data. A quality value may indicate a confidence value a user may use to rely on to determine if an experiment was successful. For example, a clearly amplified target nucleic acid in a reaction may produce a signal expected for a successful amplification. The data from this reaction may be assigned a good quality value to indicate that a user may have confidence that the data is reliable. On the other hand, a quality value indicating bad quality may indicate the processor was able to determine if amplification occurred, but there are other indications that may indicate there may have been an error. As such, a quality value indicating bad quality may indicate to a user that the data may not be as reliable.

According to various embodiments, the quality value may be indicated by an indicator. An indicator may be color, in various embodiments. As an example, good quality values may be indicated with green color and bad quality values may be indicated with a red color, with different shades of green and red to indicate a range of quality values.

Figure 2:
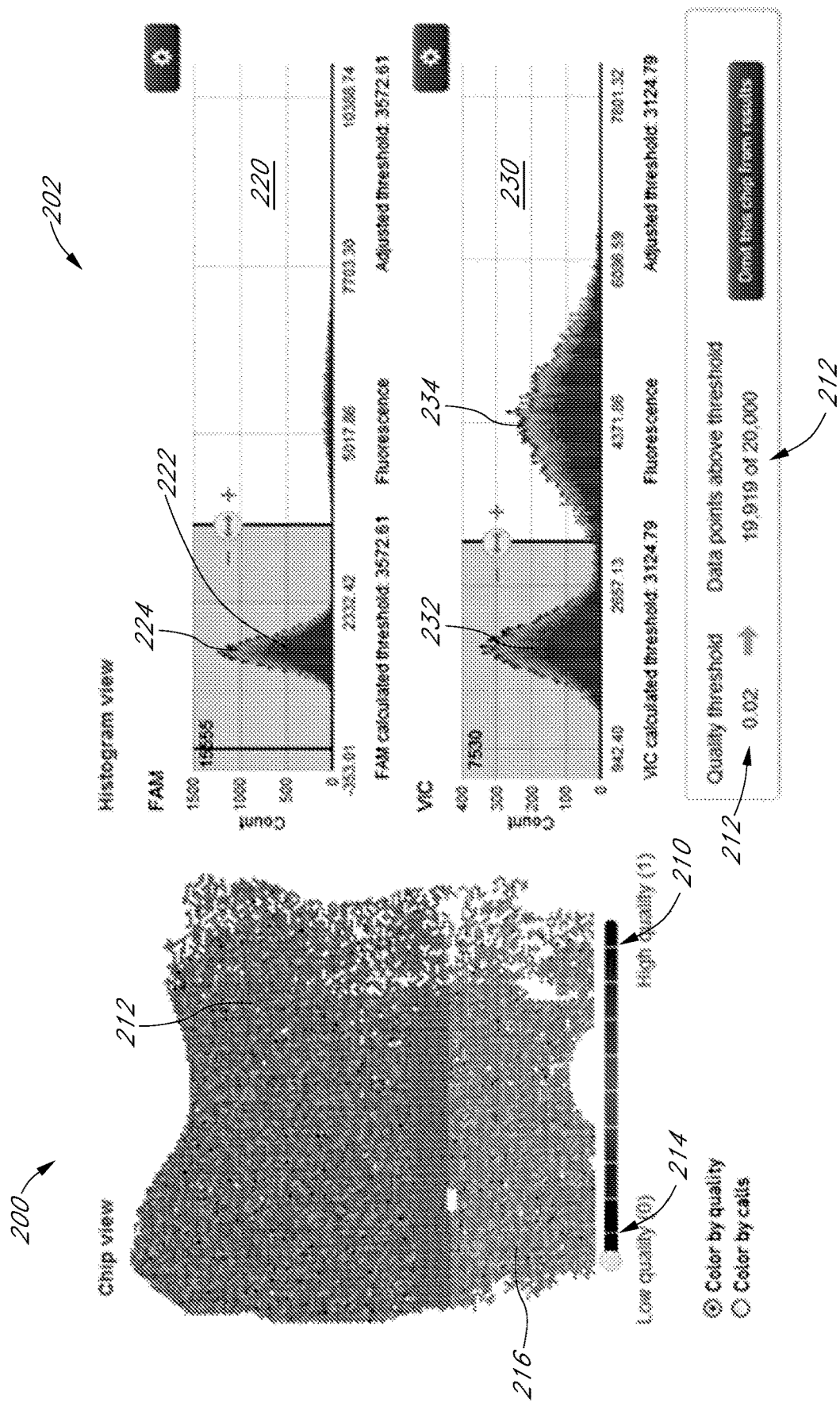
FIG. 2 illustrates a data visualization including a chip representation and histograms according to various embodiments described herein.

The system may display the quality values and associated indicator s in a spatial format. For example, as illustrated in FIG. 2, the spatial format may display the data in a representation of the chip 200. Thus, each data point is displayed in a relative location that the signal was obtained on the chip. The user is then able to visualize the data quality across the whole chip.

In the example of FIG. 2 the chip representation 200 colors a position in the two-dimensional grid with the color assigned to the quality value. The color bar under the chip representation 200 shows the indicator of high quality data 210 and the indicator of low quality data 214. Good quality data 212 is indicated by a green color in chip representation 200. Bad quality data 216 is indicated by a red color in chip representation 200. The user may be able to set a quality value threshold 212 that will change the display of data to show only the data with quality values above the quality value threshold 212. In the example illustrated in FIG. 2, the data that have a quality value above 0.02 will be displayed. Data with a quality value below 0.02 is not displayed and appear as white background in chip representation 200.

FIG. 2 also illustrates a histogram view 202 that may be displayed to a user in various embodiments. Histogram view may be viewed independently or along with chip representation 200. FAM histogram view 220 illustrates quality values as well as the call of the data. The call of data means if the system has determined the data represents positive or negative amplification of the target nucleic acid. FAM histogram view 220 indicates the positive or negative calls of data from the plurality of reaction sites of the target nucleic acid associated with FAM, while VIC histogram view 230 indicates positive or negative calls of data from the plurality of reaction sites of the target nucleic acid associated with VIC. The x-axis of FAM histogram view 220 and VIC histogram view 230 indicate the fluorescence values of a reaction site, and the y-axis indicate the number of reaction sites having a particular fluorescence value. Negative calls will have a low fluorescence value, while positive calls will have a higher fluorescence value. Thus, two peaks (one negative calls, and one positive calls) can generally be visualized by the user.

FAM histogram view 220 and VIC histogram view 230 also indicate to the user the quality values of the data. Good quality data may be indicated by a green color indicator and bad quality data may be indicated by a red color indicator.

As mentioned above, displaying chip representation 200 along with FAM histogram view 220 and VIC histogram view 230 may provide information regarding quality of the data and positive and negative calls to the user such that the user is able to adjust the set of data used to calculate information. For example, a user may be able to remove bad quality data from their experiment while at the same time balancing the quality of data with the positive and negative calls. In this way, a user can make a judgment regarding confidence and reliability of the data set. The chip representation 200, FAM histogram view 220 and VIC histogram view 230 may dynamically change to indicate a user's adjustment of quality threshold 212.

Figure 3:
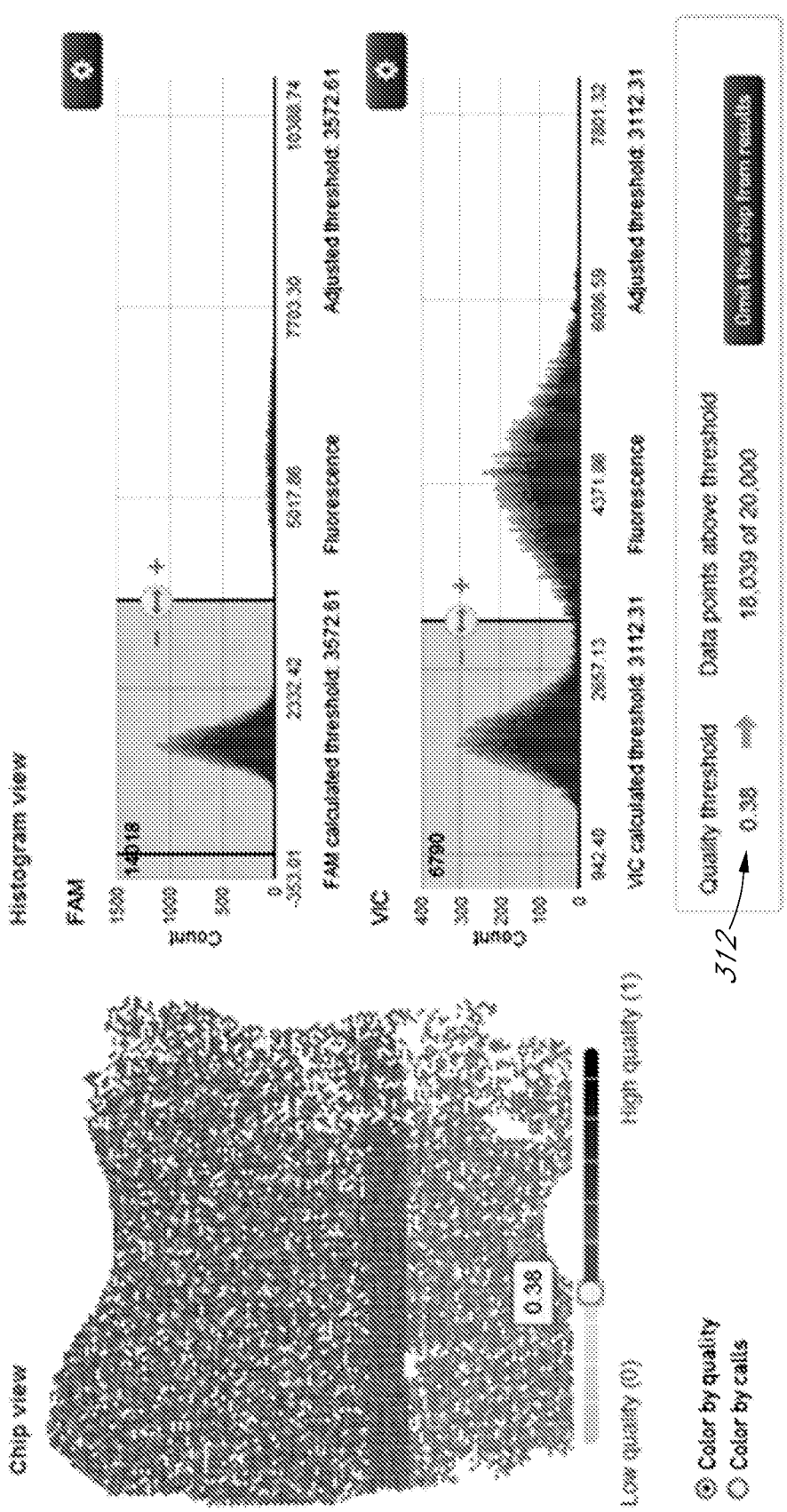
FIG. 3 illustrates a data visualization including a chip representation and histograms according to various embodiments described herein.

FIG. 3 shows the same data visualized in FIG. 2 when quality threshold 312 is raised to 0.38. It can be observed that more data points are assigned the white background color since the data with quality values lower than 0.38 are no longer displayed. The outcome of this assignment is that points that are deeper red (lower quality) have been graphically eliminated.

With reference back to FIG. 2, the FAM and VIC histogram view 220, 230 indicate the statistical distribution of FAM and VIC. The colors shown in the histograms encodes the quality value. For a given bin in the FAM histogram view 220, points within the FAM interval for that bin, the count of points with higher quality value are shown lower in the bin's graphical column and the count of points with lower quality value are shown higher up in the bin's graphical column. By doing this, it is easy to see the affects on the statistical distribution of FAM as the quality threshold is changed. For example, by raising the quality threshold, the reddish fringe riding on top of the histograms of FIG. 2 are eliminated leaving only the yellowish fringe on the top as shown in FIG. 3.

Color Coding by a Discrete Variable

Figure 4:
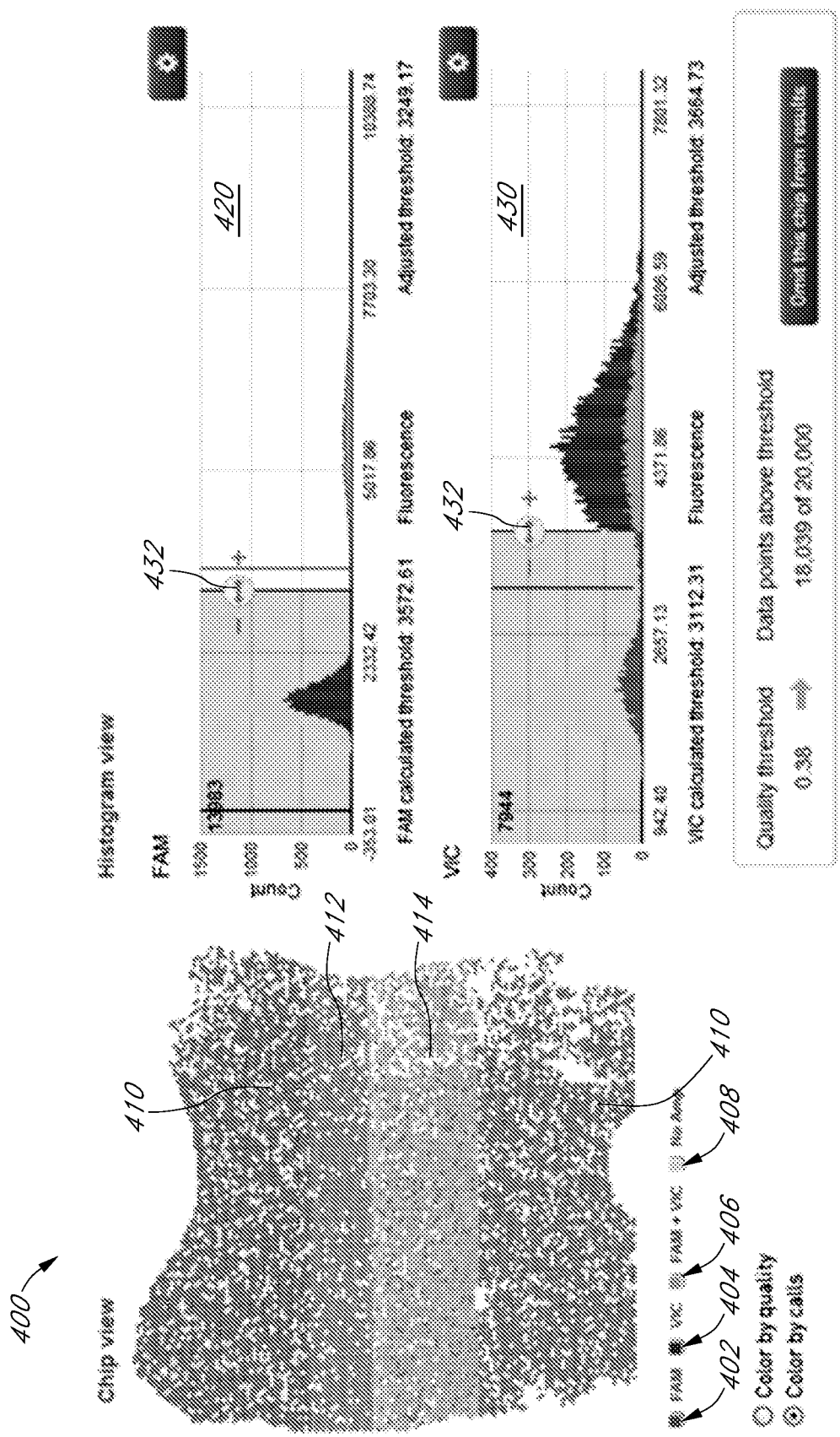
FIG. 4 illustrates data visualization including a chip representation and histograms according to various embodiments described herein.

According to various embodiments, FIG. 4 illustrates a display of the spatial distribution of the positive and negative calls as well as the statistical distribution of positive and negative calls among FAM and VIC data. In this example, indicators are used to display to a user the calls of data points from reaction sites. For example, a color indicator is displayed to the calls in a spatial format (chip representation 400) and a FAM histogram view 420 and VIC histogram view 430. Chip representation 400, FAM histogram view 420, and VIC histogram view 430 may be displayed individually or along side each other.

In FIG. 4, FAM calls are indicated by a first indicator 402, VIC calls are indicated by a second indicator 404, reactions sites including both FAM and VIC signals are indicated by a third indicator 406, and negative calls are indicator by a fourth indicator 408. The indicators in some embodiments may be different colors.

Figure 5:
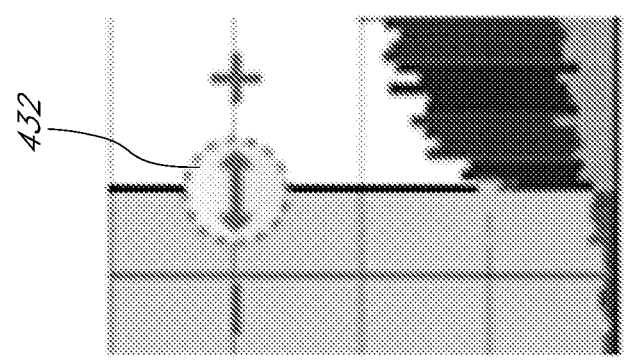
FIG. 5 illustrates a slider bar according to various embodiments described herein.

In the example of FIG. 4, chip representation 400 shows that there is several data points with FAM and VIC signals in area 412 of chip representation 400. Area 412 appears to be a strip in the center of chip representation 400. Further, most VIC calls appear in areas 410 of chip representation 400. Area 414 shows several negative calls. In dPCR, the expectation is that all of these types of calls (positive for VIC, positive for FAM, positive for VIC and FAM, and negative calls) should be uniformly distributed across the substrate rather than clumped in various areas as shown in FIG. 4. This way, the user is able to visualize the types of calls and perhaps come to the conclusion that there is something wrong with this data set. Further, the user may then look to FAM histogram view 420 and VIC histogram 430 and confirm their conclusion that there are several errors within this data. The FAM and VIC histogram views 420 and 430 also include a slider button 432, adjustable by the user. The user, when viewing the display of FIG. 4, may realize that the fluorescence threshold the processor has used to determine positive and negative calls is not accurate. The user may then adjust the slider button to where they believe the fluorescence threshold should be and the processor will then recalculate the results. The slider button 432 is illustrated in FIG. 5.

Figure 6:
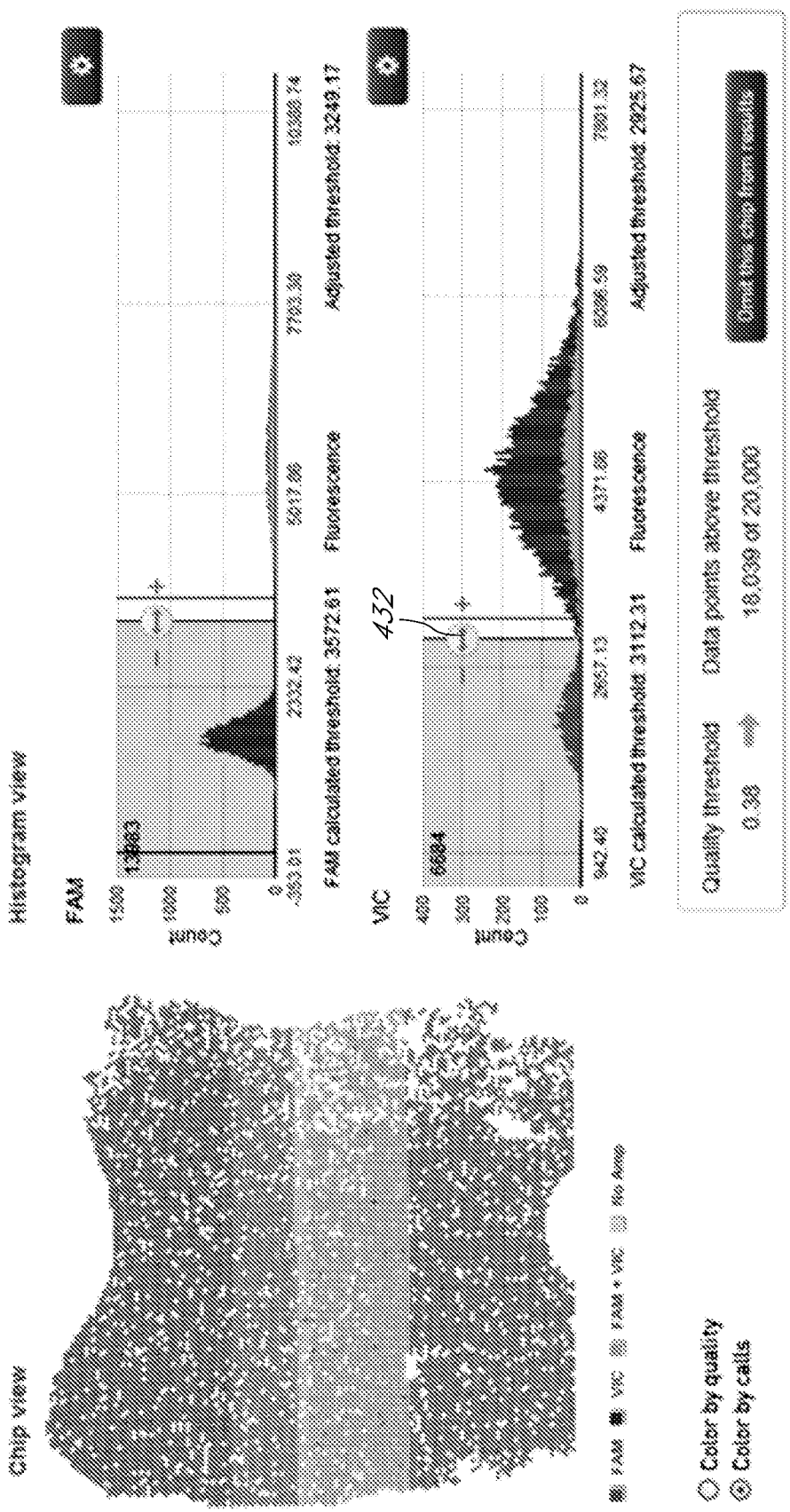
FIG. 6 illustrates data visualization including a chip representation and histograms according to various embodiments described herein.

With reference back to FIG. 4, slider button 432 on VIC histogram view 430 appears to be in an incorrect position. The user may select slider button 432 and adjust it to the left so that the fluorescence threshold to determine positive and negative calls is at a lower fluorescence level than previously set. FIG. 6 illustrates a more accurate fluorescence threshold.

Scatter Plot Views

Figure 7:
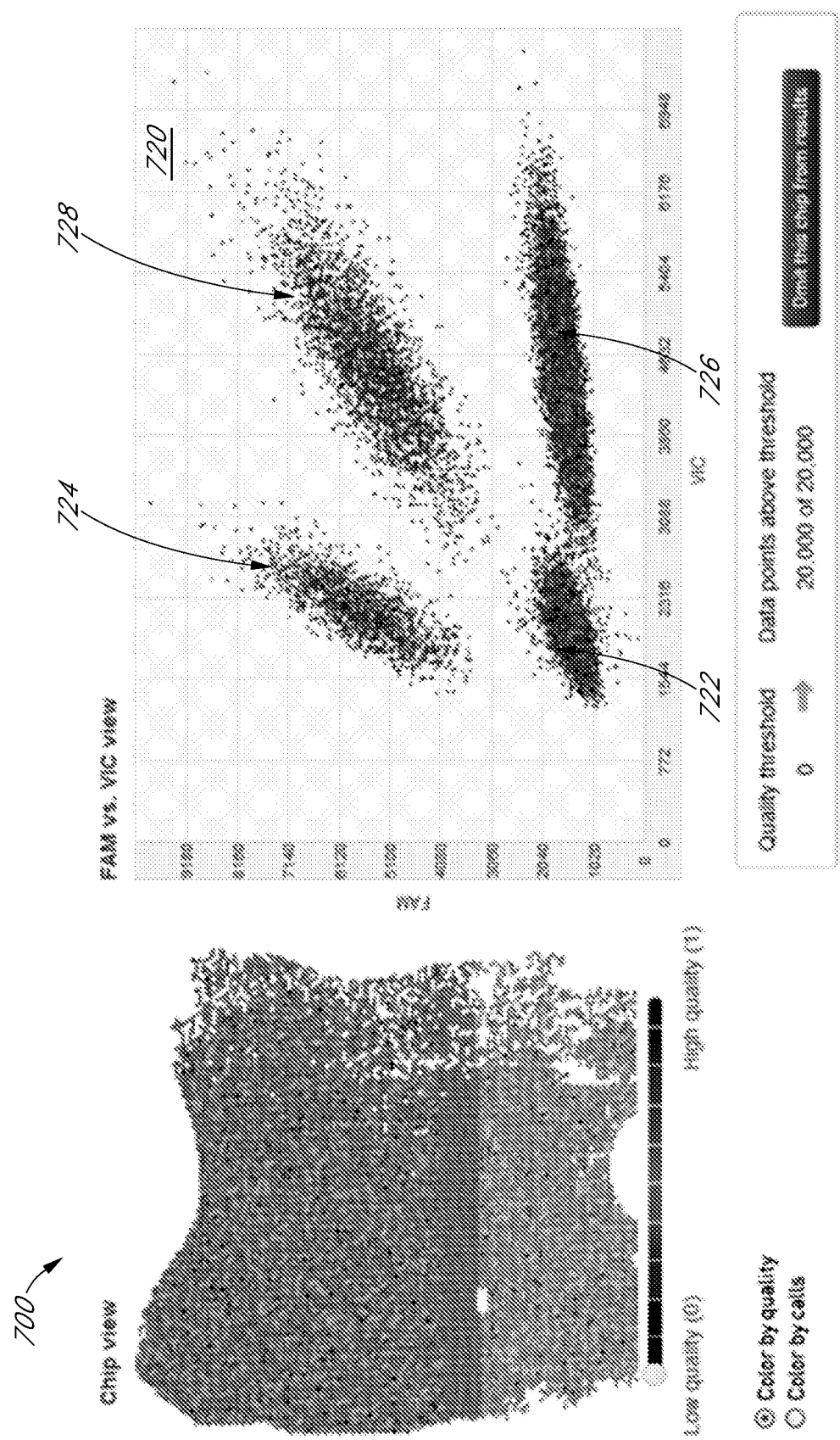
FIG. 7 illustrates a data visualization including a chip representation and a scatter plot according to various embodiments described herein.

According to various embodiments of the present teaching, statistical characteristics of the data can also be shown using a scatter plot. For example, with a scatter plot, quality values, as well as VIC and FAM fluorescence calls may be visualized. FIG. 7 illustrates a chip representation 700 and a scatter plot 720. Chip representation 700 and scatter plot 720 may be displayed separately as well as alongside each other.

Scatter plot 720 has a y-axis that indicates FAM fluorescence value and a x-axis that indicates VIC fluorescence value. If data from a reaction site indicates no amplification, FAM and VIC fluorescence should be at a minimal value. As such, the data point will be displayed in the lower left corner of scatter plot 720. The data point cluster 722 indicates data that may be determined to be negative calls, or have no amplification for its respective reaction sites.

If a reaction site had only amplification of the target nucleic acid labeled with the FAM dye, the fluorescence value of FAM (y-axis) will be present, but the VIC signal (x-axis) will be minimal. Thus, the data points associated with reaction sites emitting FAM fluorescence will be displayed in the upper left corner of scatter plot 720. Data cluster 724 indicates data points associated with reaction sites emitting FAM fluorescence.

Similarly, if a reaction site had amplification of only the target nucleic acid labeled with VIC, the FAM fluorescence value (y-axis) will be minimal while the VIC fluorescence value (x-axis) will be significant. Thus, the data points associated with reaction sites emitting VIC fluorescence will be displayed in the lower right corner of scatter plot 720. Data cluster 726 indicates data points associated with reaction sites emitting VIC fluorescence.

If a reaction site contains both the target nucleic acid associated with FAM and the target nucleic acid associated with VIC, both FAM and VIC fluorescent signals will be significant. As such, data points associated with reaction sites emitting both FAM and VIC will be displayed in the upper right corner of scatter plot 720. As such, data cluster 728 indicates data points associated with reaction sites emitting FAM and VIC fluorescence.

Figure 8:
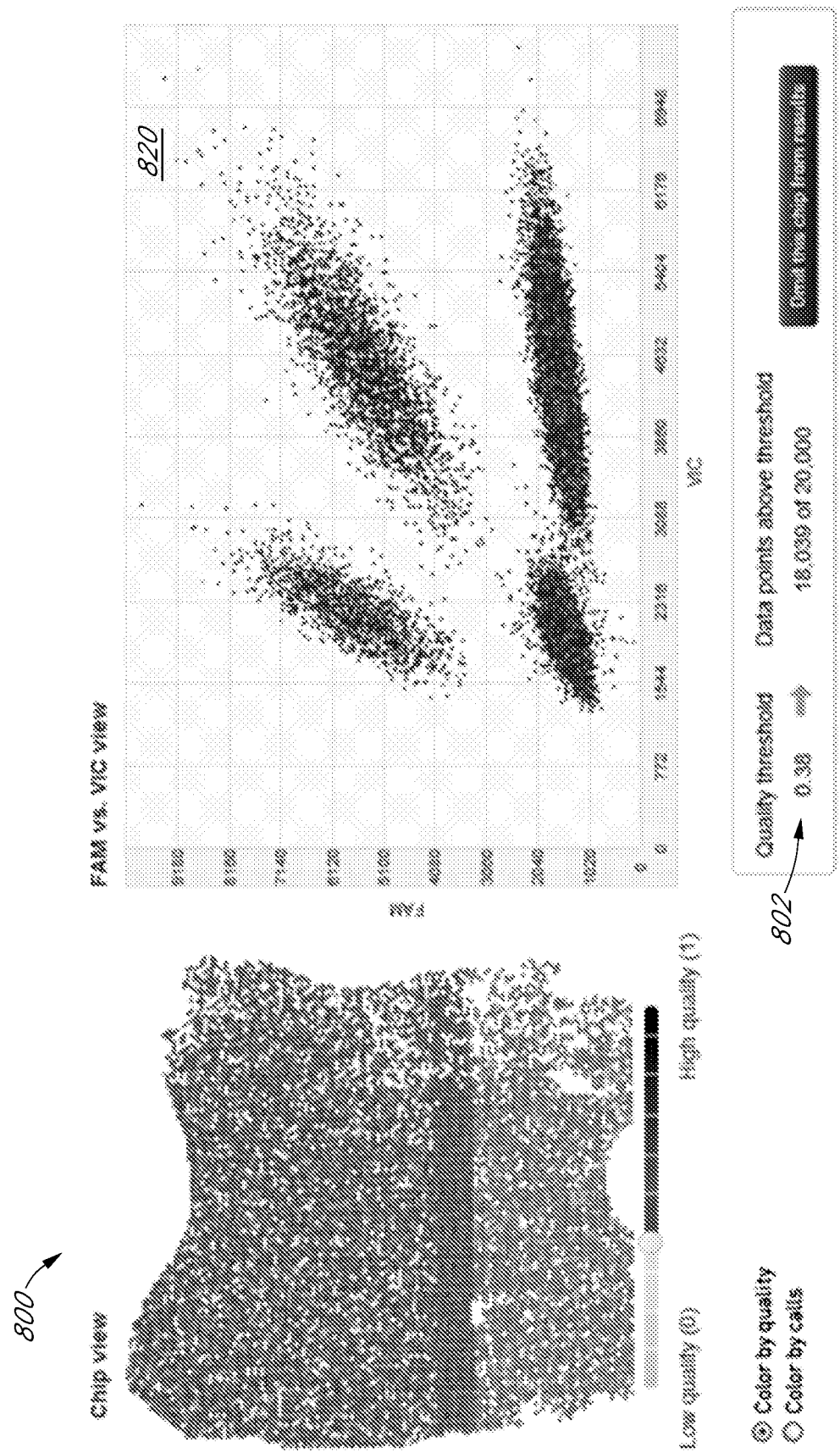
FIG. 8 illustrates a data visualization including a chip representation and a scatter plot according to various embodiments described herein.

FIG. 7 also illustrates that the data displayed is above a quality level of 0. A quality threshold may be changed by the user. FIG. 8 shows data points that have a quality value over 0.38 because the quality threshold 802 has been set at 0.38. Data points below the quality threshold 802 are removed from chip representation 800 and also scatter plot 820.

Figure 9:
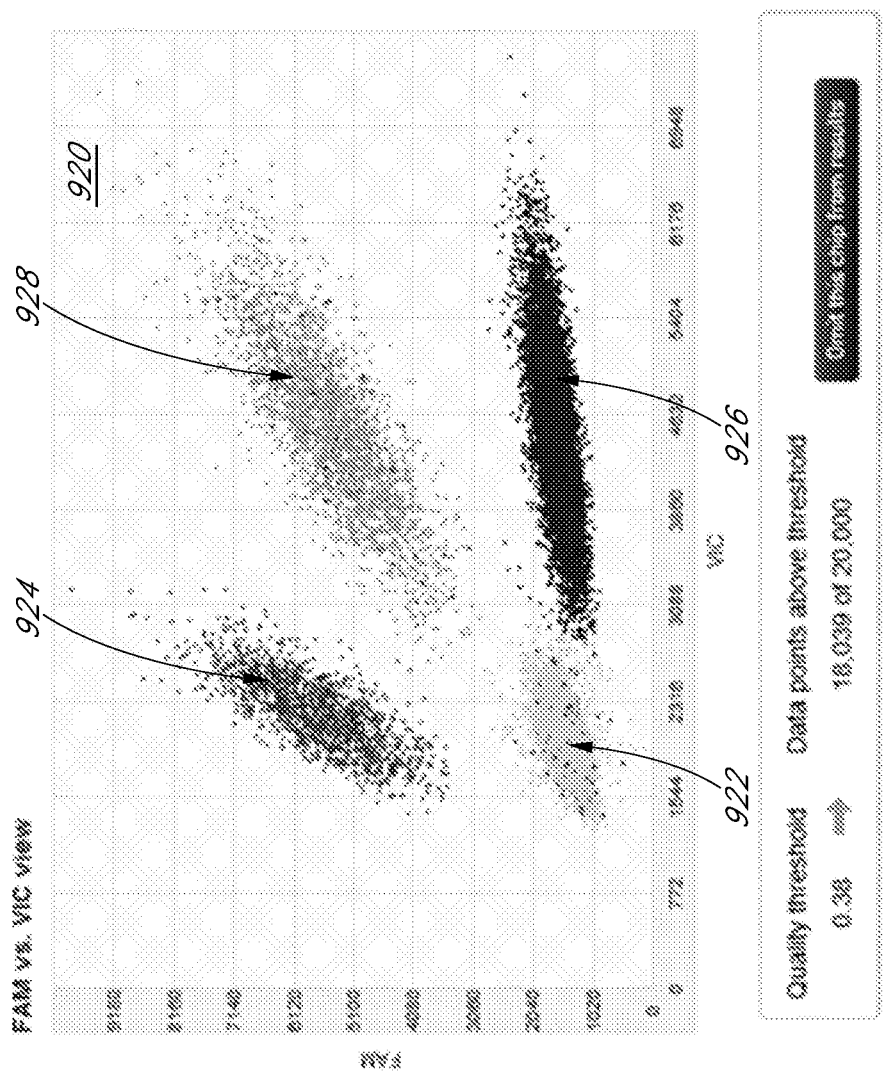
FIG. 9 illustrates a data visualization including a chip representation and a scatter plot according to various embodiments described herein.
Figure 9:
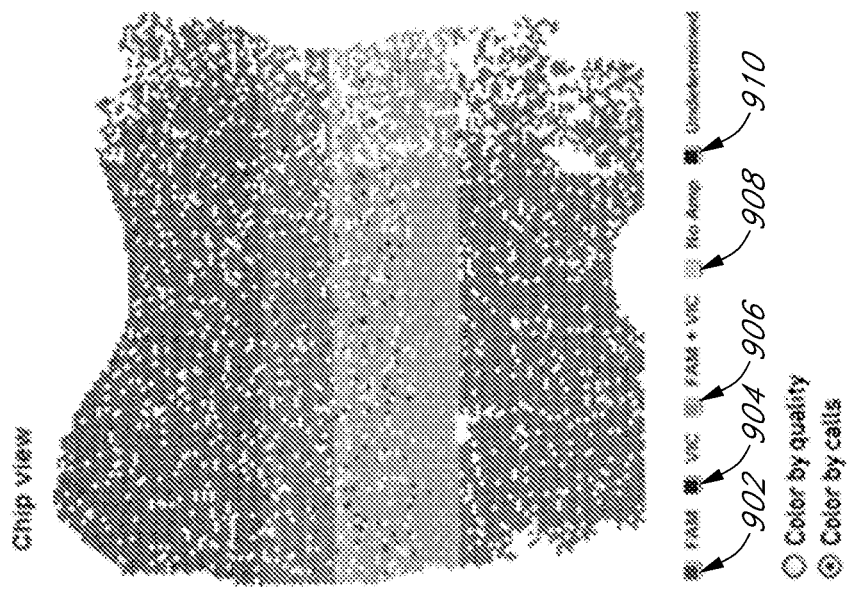

FIG. 9 shows the same data displayed in chip view 800 and scatter plot 820, but the indicator has changed to indicate the positive or negative call of each data point. In FIG. 9, FAM calls are indicated by a first indicator 902, VIC calls are indicated by a second indicator 904, reactions sites including both FAM and VIC signals are indicated by a third indicator 906, negative calls are indicator by a fourth indicator 908, and reaction sites where the call could not be determined by the processor are indicated by a fifth indicator 910. The indicators in some embodiments may be different colors.

Scatter plot 920 has a y-axis that indicates FAM fluorescence value and a x-axis that indicates VIC fluorescence value. If data from a reaction site indicates no amplification, FAM and VIC fluorescence should be at a minimal value. As such, the data point will be displayed in the lower left corner of scatter plot 920. The data point cluster 922 indicates data that may be determined to be negative calls, or have no amplification for its respective reaction sites. The data points in data cluster 922 mostly show fourth indicator 908.

If a reaction site had only amplification of the target nucleic acid labeled with the FAM dye, the fluorescence value of FAM (y-axis) will be present, but the VIC signal (x-axis) will be minimal. Thus, the data points associated with reaction sites emitting FAM fluorescence will be displayed in the upper left corner of scatter plot 920. Data cluster 924 indicates data points associated with reaction sites emitting FAM fluorescence. The data points in data cluster 924 mostly show first indicator 902.

Similarly, if a reaction site had amplification of only the target nucleic acid labeled with VIC, the FAM fluorescence value (y-axis) will be minimal while the VIC fluorescence value (x-axis) will be significant. Thus, the data points associated with reaction sites emitting VIC fluorescence will be displayed in the lower right corner of scatter plot 920. Data cluster 926 indicates data points associated with reaction sites emitting VIC fluorescence. The data points in data cluster 926 mostly show second indicator 904.

If a reaction site contains both the target nucleic acid associated with FAM and the target nucleic acid associated with VIC, both FAM and VIC fluorescent signals will be significant. As such, data points associated with reaction sites emitting both FAM and VIC will be displayed in the upper right corner of scatter plot 920. As such, data cluster 928 indicates data points associated with reaction sites emitting FAM and VIC fluorescence. The data points in data cluster 928 mostly show third indicator 908.

A user utilizing scatter plot 920 may be able to determine whether the calls were assigned correctly.

Figure 10:
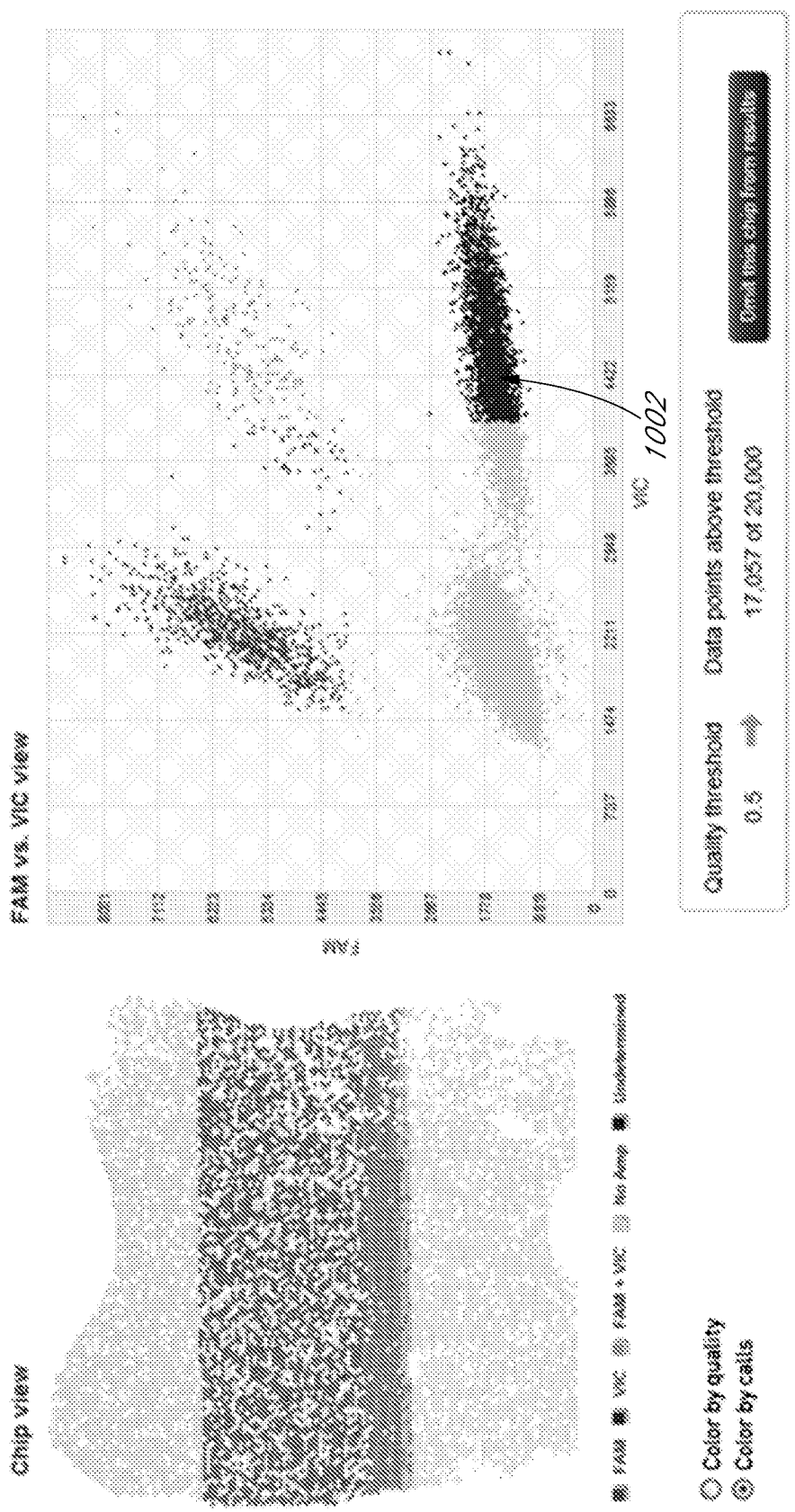
FIG. 10 illustrates a data visualization including a chip representation and a scatter plot according to various embodiments described herein.

FIG. 10 shows color by call where it is clear that calls have been assigned incorrectly. Each cluster of points in the figure should mostly show one indicator type if calls are assigned correctly. In cluster 1002, at least two different indicators are prominent. As such, the user may be able to determine there may be a problem with the data set displayed.

Figure 11:
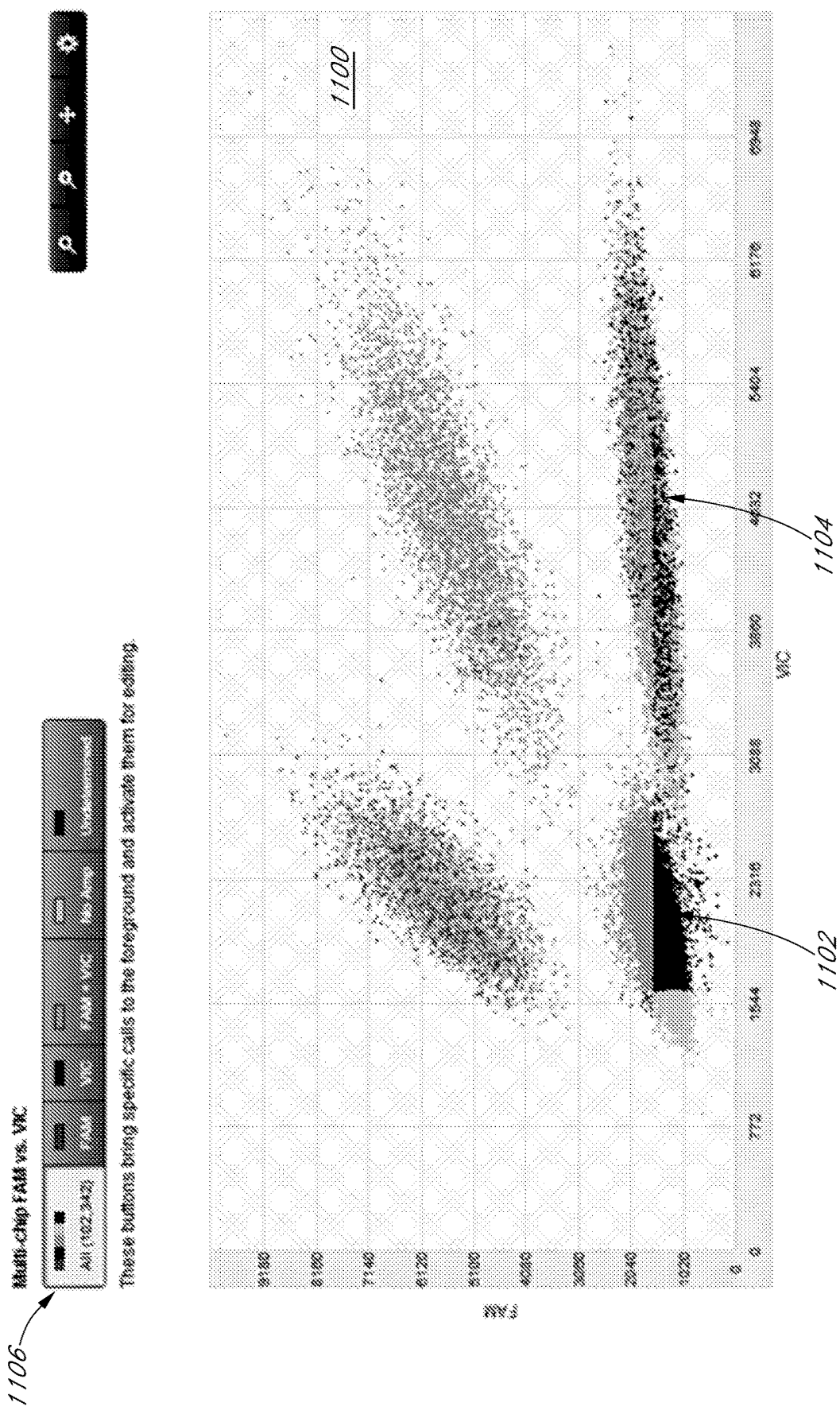
FIG. 11 illustrates a data visualization including a scatter plot according to various embodiments described herein.

FIG. 11 also illustrates another scatter plot 1100. Data cluster 1102 and data cluster 1104 both have a significant amount of at least two indicators. A user viewing scatter plot 1100 will be able to determine the calls are not correct or there were errors in the experiment that generated the data.

Various embodiments of the present disclosure give a user the ability to quickly spot anomalies in the data. For example, the user would be alerted that there was a systemic issue with their experimental procedures if, for example, in FIG. 2, the low quality values were not distributed throughout the histograms but were localized to one area of chip representation 200 or one area of the histogram views 220 and 230. Similarly, the call distribution as illustrated in FIG. 3 is not probable without some error in the data or experiment. As such, embodiments of the present disclosure allow for visualization of a large quantity of data points and allow a user to determine useful information from the data quickly and easily.

Further, embodiments of the present disclosure allow a user to view data based on quality values. In this way, the consequences of rejecting data based on a quality can be anticipated and quickly observed.

One downside of viewing a dense two-dimensional scatter plots is that points are plotted on top of each other. This means points with one value assigned could completely hide points that have another and incorrect value assigned. FIG. 11 shows a case where there should be four clusters of clearly separated points, each cluster having a uniform color. The control on top of the figure provides a mechanism to get around the hidden point problem. In FIG. 11, the "All" option 1106 is selected. This means all data points are in the foreground and will be affected by graphical tools used to encircle and override calls assigned to the points.

Figure 12:
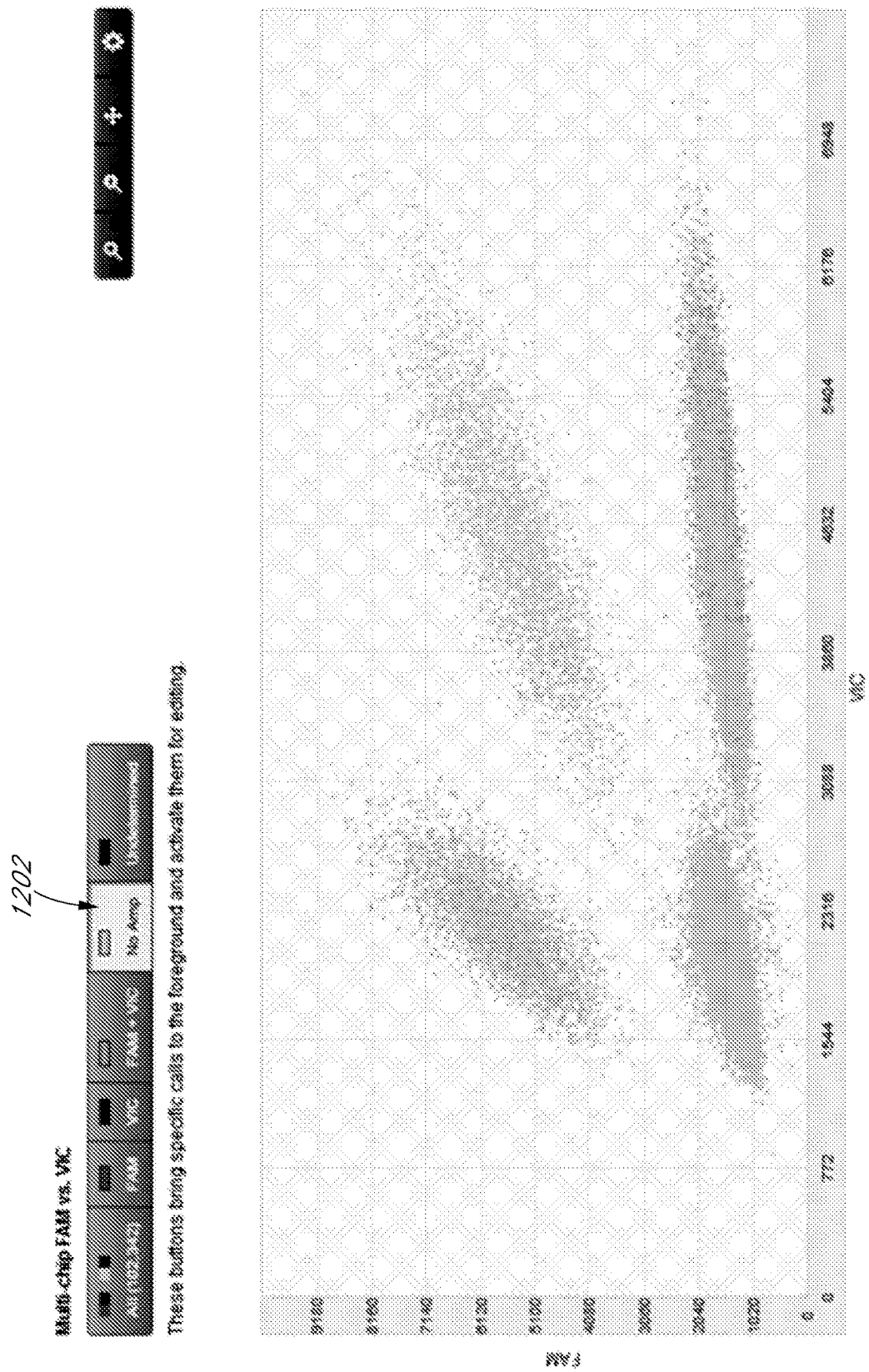
FIG. 12 illustrates a data visualization including a scatter plot according to various embodiments described herein.

FIG. 12 illustrates the data points displayed if the "No Amp" option 1202 is selected. Only the points where a negative call, or no amplification of a target nucleic acid, was determined are displayed.

Figure 13:
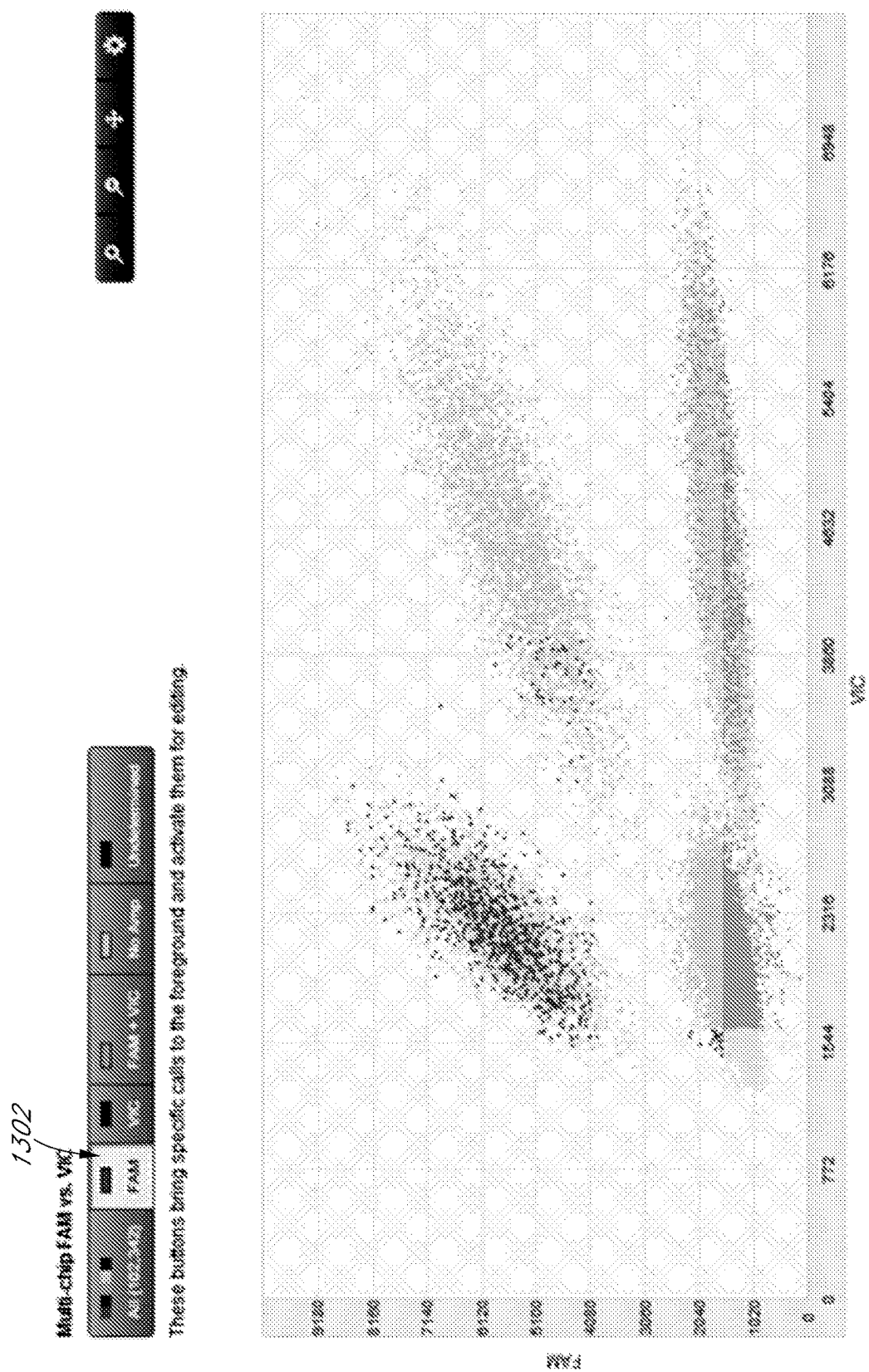
FIG. 13 illustrates a data visualization including a scatter plot according to various embodiments described herein.

FIG. 13 shows the same data where the "FAM" option 1302 is selected. Comparing FIGS. 12 and 13, it is apparent that many "No Amp" points are hidden in FIG. 12. By bringing all the "No Amp" points to the foreground, all of them are exposed and are activated for overriding call assignments using graphical tools. The user can be assured that all points initially assigned the "No Amp" call have been corrected (once the user has done so). The user would then continue to select the other calls and correct calls where needed. After moving through all call types the user can be assured that all calls are correct.

Methods and systems according to various embodiments may allow a user to quickly and easily view quality and calls without the time and effort needed to analyze every data point using other methods. If the user were to only have the option shown in FIG. 11 where the "All" option is selected, the user would be obligated to encircle each region of points whether or not there appeared to be incorrect calls in the region and assign the correct call value to that region. By having the option to only bring to the foreground one call at a time, the user might only need to perform manual corrections on a small part of the graph. FIG. 13 shows that for the case of the "FAM" call, only two small areas of points need to be corrected.

Although the present invention has been described with respect to certain exemplary embodiments, examples, and applications, it will be apparent to those skilled in the art that various modifications and changes may be made without departing from the invention.

What is claimed is:

1. A computer-implemented method for generating a data visualization for operating a digital polymerase chain reaction (dPCR) system, the method comprising:
   receiving fluorescent emission data, obtained by a detector, the fluorescent emission data comprising a plurality of data points corresponding to fluorescence emission from a plurality of reaction sites of a substrate, the fluorescent emission data indicative of presence or absence of amplification product of a dPCR reaction at the plurality of reaction sites;
   determining a first set of data points of the plurality of data points is of a first data quality level based on a quality threshold;
   determining a second set of data points of the plurality of data points is of a second data quality level based on the quality threshold;
   displaying together on a user interface a first data visualization and a second data visualization, wherein:
   the first data visualization displays the plurality of data points in a spatial representation of the substrate such that each data point is displayed at a relative spatial location of its corresponding reaction site of the plurality of reaction sites of the substrate, the first set of data points being displayed with a first indication and the second set of data points being displayed with a second indication differing from the first indication, and
   the second data visualization displays a histogram containing the first and second sets of data points, wherein:
   a first axis of the histogram represents fluorescence emission value,
   a second axis of the histogram represents a number of reaction sites,
   the first set of data points are displayed with the first indication, and
   the second set of data points are displayed with the second indication;
   adjusting the quality threshold to an adjusted quality threshold; and
   changing the first and second data visualizations displayed on the user interface based on the adjusted quality threshold.

2. The method of claim 1, wherein the first and second indications differ in color.

3. The method of claim 1, wherein the first data quality level and second data quality level each comprises a range of data quality values.

4. The method of claim 1, wherein the histogram displays a first peak of the data points corresponding to emission data indicating absence of amplification product and displays a second peak corresponding to emission data indicating presence of amplification product.

5. A digital polymerase chain reaction (dPCR) system, the system comprising:
   a memory; and
   a processor for:
   receiving fluorescent emission data, obtained by a detector, the fluorescent emission data comprising a plurality of data points corresponding to fluorescence emission from a plurality of reaction sites of a substrate, the fluorescent emission data indicative of presence or absence of amplification product of a dPCR reaction at the plurality of reaction sites;
   determining a first set of data points of the plurality of data points is of a first data quality level based on a quality threshold;
   determining a second set of data points of the plurality of data points is of a second data quality level based on the quality threshold;
   displaying together on a user interface a first data visualization and a second data visualization, wherein:
   the first data visualization displays the plurality of data points in a spatial representation of the substrate such that each data point is displayed at a relative spatial location of its corresponding reaction site of the plurality of reaction sites of the substrate, the first set of data points being displayed with a first indication and the second set of data points being displayed with a second indication differing from the first indication, and the second data visualization displays a histogram containing the first and second sets of data points, wherein:

a first axis of the histogram represents fluorescence emission value, a second axis of the histogram represents a number of reaction sites, the first set of data points are displayed with the first indication, and the second set of data points are displayed with the second indication;

adjusting the quality threshold to an adjusted quality threshold; and changing the first and second data visualizations displayed on the user interface based on the adjusted quality threshold.

6. The system of claim 5, wherein the first and second indications differ in color.

7. The system of claim 5, wherein the first data quality level and second data quality level each comprises a range of data quality values.

8. The system of claim 5, wherein the histogram displays a first peak corresponding to emission data indicating absence of amplification product and displays a second peak corresponding to emission data indicating presence of amplification product.

9. A non-transitory computer-readable storage medium encoded with instructions, executable by a processor, for generating a data visualization for a digital polymerase chain reaction (dPCR) system, the instructions including instructions for:

receiving fluorescent emission data, obtained by a detector, the fluorescent emission data comprising a plurality of data points corresponding to fluorescence emission from a plurality of reaction sites of a substrate, the fluorescent emission data indicative of presence or absence of amplification product of a dPCR reaction at the plurality of reaction sites;

determining a first set of data points of the plurality of data points is of a first data quality level based on a quality threshold;

determining a second set of data points of the plurality of data points is of a second data quality level based on the quality threshold;

displaying together on a user interface a first data visualization and a second data visualization, wherein:

the first data visualization displays the plurality of data points in a spatial representation of the substrate such that each data point is displayed at a relative spatial location of its corresponding reaction site of the plurality of reaction sites of the substrate, the first set of data points being displayed with a first indication and the second set of data points being displayed with a second indication differing from the first indication, and the second data visualization displays a histogram containing the first and second sets of data points, wherein:

a first axis of the histogram represents fluorescence emission value, a second axis of the histogram represents a number of reaction sites, the first set of data points are displayed with the first indication, and the second set of data points are displayed with the second indication;

adjusting the quality threshold to an adjusted quality threshold; and changing the first and second data visualizations displayed on the user interface based on the adjusted quality threshold.

10. The non-transitory computer-readable storage medium of claim 9, wherein the first and second indications differ in color.

11. The non-transitory computer-readable storage medium of claim 9, wherein the first data quality level and second data quality level each comprises a range of data quality values.

12. The non-transitory computer-readable storage medium of claim 9, wherein the histogram displays a first peak corresponding to emission data indicating absence of amplification product and displays a second peak corresponding to emission data indicating presence of amplification product.

13. The method of claim 1, wherein the reaction sites are spatially disposed in a two-dimensional array.

14. The method of claim 1, wherein the first and second data quality levels are above the quality threshold and a third set of data points has a third data quality level below the quality threshold, the third set of data points displayed in the first data visualization with a third indication.

15. The system of claim 5, wherein the first and second data quality levels are above the quality threshold and a third set of data points has a third data quality level below the quality threshold, the third set of data points displayed in the first data visualization with a third indication.

16. The non-transitory computer-readable storage medium of claim 9, wherein the first and second data quality levels are above the quality threshold and a third set of data points has a third data quality level below the quality threshold, the third set of data points displayed in the first data visualization with a third indication.

17. The method of claim 1,
wherein:
the plurality of data points correspond to fluorescence emission from a first fluorescent dye and a second fluorescent dye, the first and second sets of data points correspond to fluorescence emission from the first fluorescent dye, and a third and fourth set of data points of the plurality of data points correspond to fluorescence emission from the second fluorescent dye; and the method further comprising:

determining the third set of data points by determining the third set of data points is of the first data quality level based on the quality threshold, determining the fourth set of data points by determining the fourth set of data points is of the second data quality level based on the quality threshold, displaying together on the user interface with the first and second data visualization a third data visualization wherein:

the first data visualization displays the third set of data points with the first indication and the fourth set of data points with the second indication, and the third data visualization displays a second histogram, the histogram being a first histogram, the second histogram containing the third and fourth sets of data points, wherein:
a first axis of the second histogram represents fluorescence emission value,
a second axis of the second histogram represents a number of reaction sites,
the third set of data points is displayed with the first indication, and
the fourth set of data points is displayed with the second indication, and
changing the second histogram displayed on the user interface based on the adjusted quality threshold.

18. The method of claim 17, wherein the first and second data quality levels are above the quality threshold and a fifth set of data points has a third data quality level below the quality threshold, the fifth set of data points displayed in the first visualization with a third indication.

19. The method of claim 17, wherein the first fluorescent dye is FAM and the second fluorescent dye is VIC.

* * * * *